United States Patent [19]

McElligott

[11] Patent Number: 4,794,203

[45] Date of Patent: Dec. 27, 1988

[54] HYDROHALOGENATION OF MYRCENE IN THE PRESENCE OF ORGANIC AMINES

[75] Inventor: Lois T. McElligott, Abington, Pa.

[73] Assignee: Union Camp Corporation, Wayne, N.J.

[21] Appl. No.: 749,881

[22] Filed: Jun. 27, 1985

Related U.S. Application Data

[63] Continuation-in-part of Ser. No. 515,563, Jul. 20, 1983.

[51] Int. Cl.$^4$ .............................................. C07C 17/08
[52] U.S. Cl. .................................................... 570/231
[58] Field of Search ......................................... 570/231

[56] References Cited

U.S. PATENT DOCUMENTS

| | | | |
|---|---|---|---|
| 2,242,084 | 5/1941 | Nicodemus et al. | 570/236 |
| 2,871,271 | 1/1959 | Booth | 570/231 |
| 3,016,408 | 1/1962 | Webb | 570/231 |
| 3,055,954 | 9/1962 | Montagna et al. | 570/231 |
| 3,993,586 | 11/1976 | Hagedorn et al. | 570/231 |
| 4,049,730 | 9/1977 | Boggs | 570/249 |

FOREIGN PATENT DOCUMENTS

| | | | |
|---|---|---|---|
| 1768544 | 5/1968 | Fed. Rep. of Germany | 570/231 |
| 798889 | 7/1958 | United Kingdom | 570/236 |

*Primary Examiner*—Howard T. Mars
*Attorney, Agent, or Firm*—E. J. Sites

[57] ABSTRACT

The disclosure is of an improved process for the hydrohalogenation of myrcene in the presence of a catalyst, which comprises carrying out the hydrohalogenation at a temperature below 25° C. in the presence of an organic amine.

10 Claims, 1 Drawing Sheet

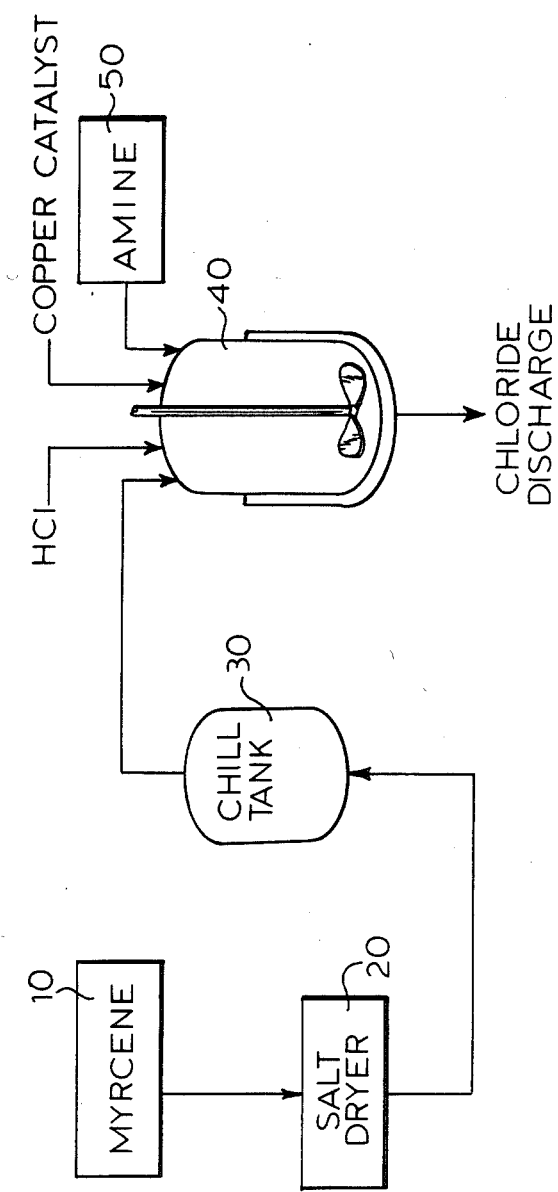

HYDROHALOGENATION OF MYRCENE IN THE PRESENCE OF ORGANIC AMINES

CROSS-REFERENCE TO RELATED APPLICATION

This application is a continuation-in-part of copending U.S. application Ser. No. 515,563 filed July 20, 1983.

BACKGROUND OF THE INVENTION

1. Field of the Invention

The invention related to processes for the hydrohalogenation of myrcene.

2. Brief Description of the Prior Art

The literature is replete with descriptions of processes for the hydrohalogenation of conjugated dienes. Representative of such descriptions are those found in the U.S. Pat. Nos. 2,882,323 and 3,016,408 and in British Pat. No. 896,262; see also German Offenlegungsschrift 1,768,544. In the latter patent, hydrohalogenation of butadiene is conducted in the presence of aqueous mixtures including organic amines. The reaction mixtures are corrosive and in some reactions would tend to promote solvolysis. The German Auslegeschrift 1,253,264 describes the hydrochlorination of butadiene in a gas phase reaction. The present invention is an improvement over the prior art processes in that it may be carried out in liquid phases of the reactants, at low temperatures and with minimal solvolysis of products. Improved yields are obtained of the desired products.

The present invention is advantageous when used to hydrochlorinate myrcene. Myrcene is a conjugated diene of the formula:

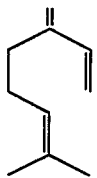

(I)

When hydrochlorinated in the absence of any catalyst, the major product is myrcenyl chloride. However, the commercially valuable products of myrcene hydrochlorination are the associated co-products, namely, geranyl chloride and neryl chloride. Hydrochlorination in the presence of a copper-containing catalyst shifts the reaction in favor the desired co-products. It has been postulated that the hydrochlorination of myrcene in the presence of a copper catalyst proceeds according to the reaction scheme:

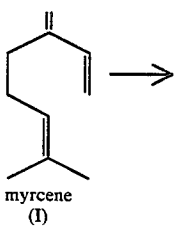

myrcene
(I)

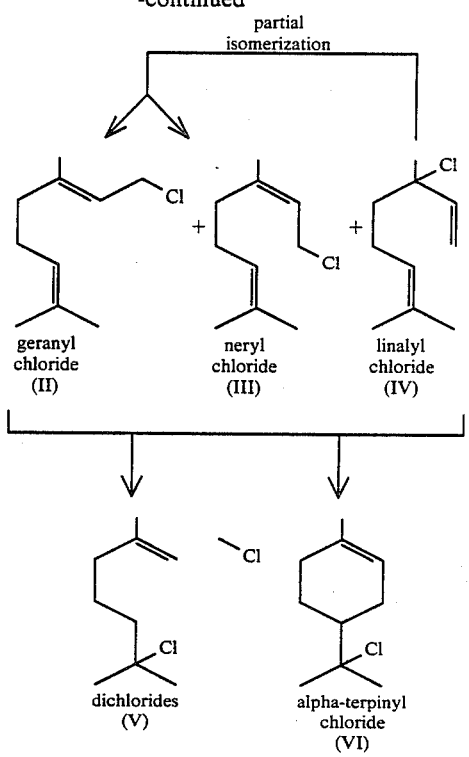

Cyclization may also undesirably occur to form the alpha-terpinyl chlorides, especially at reaction temperatures in excess of 25° C.

When the copper catalyst employed is in the form of cupric chloride (CuCl$_2$) the products generally include substantial proportions of linalyl chloride and lesser proportions of the desired geranyl and neryl chlorides. When the copper catalyst is in the form of cuprous chloride, the linalyl chloride product is lessened due, apparently, to partial isomerization to the desired geranyl and neryl chlorides.

From the above proposed reaction scheme, it will be appreciated that any process for hydrochlorination of myrcene, to be commercially feasible, must result in a favorable yield of the desired geranyl (II) and neryl (III) monochlorides and minimal formation of linalyl (IV) and alpha-terpinyl (VI) monochlorides. It was previously appreciated that the relative proportions of monochlorides (II), (III) and (IV) in the hydrochlorination product reaction mixture could be controlled to some degree by selection of the reaction temperature, gas flow-rate and catalyst concentration.

We have now found that when the prior art hydrohalogenation of myrcene (U.S. Pat. No. 2,871,271), is carried out in the presence of a particular kind of organic amine, then the isomerization of the linalyl chloride product during the hydrohalogenation reaction is shifted to favor formation of the less-substituted allylic chloride, being geranyl chloride (II) and neryl chloride (III).

While it is known to include certain organic amines in combination with copper in a catalyst for hydrochlorination of a simple diene such as butadiene (U.S. Pat. No. 3,993,586 to Hagedorn, et al), these amines fail to increase the yield of neryl and geranyl halides when applied to the hydrohalogenation of myrcene, even when used under anhydrous conditions. It is also known that certain organic amines can be employed in combination with copper to isomerize allylic halides to their allylic isomers (British Pat. No. 798,889 to Young), but only at elevated temperatures. These amines also fail to increase the yield of neryl and geranyl halides when applied to the hydrohalogenation of myrcene, even when used at the lower temperatures necessary in this reaction to avoid extensive yield losses due to rearrangement to terpinyl halides.

The advantages associated with the improved process of the invention include improved overall yield of the more desirable neryl and geranyl chlorides from myrcene and a greater selectivity of the more important geranyl isomer.

SUMMARY OF THE INVENTION

The invention comprises, a novel method for the hydrohalogenation of myrcene comprising hydrohalogenating myrcene under anhydrous, liquid-phase conditions in the presence of a copper-containing hydrohalogenation catalyst, and further comprising carrying out the hydrohalogenation at a temperature below 25° C. in the presence of an organic amine which is selected from the group consisting of secondary and tertiary amines containing at least two hydrocarbyl groups of six or more carbon atoms each.

The improved process of the invention may be carried out in a batch or a continuous manner.

BRIEF DESCRIPTION OF THE DRAWING

The drawing is a schematic representation of a preferred embodiment method of the invention.

DETAILED DESCRIPTION OF THE PREFERRED EMBODIMENTS OF THE INVENTION

The method of the invention is employed advantageously for the hydrohalogenation of myrcene to obtain the geranyl and neryl halides which are intermediates for the manufacture of commercially valuable geraniol and nerol. The improved method of the invention will increase the overall yield of the geranyl and neryl halides over the prior art processes and will improve selectivity of the ratio of geranyl isomer to the neryl isomer. Commerically available myrcene made by pyrolysis of beta-pinene, purified forms of myrcene, and myrcene isolated frmm natural materials may be provided as the starting material in the preferred process of the invention.

The accompanying drawing is a schematic representation of a preferred embodiment method of the invention for the hydrochlorination of myrcene. As shown in the Figure the provided myrcene initially held in tank 10 may be first dried in a conventional salt bed dryer 20 to remove water, as necessary. The dried myrcene is then preferably cooled to a temperature in the range of from about −30° C. to about 25° C.; most preferably circa 10° C. in a cooling unit 30. Alternatively, the myrcene may be cooled first and then processed through a salt bed dryer 20 to remove water. Cooling the starting myrcene prior to drying in the salt bed dryer 20 is somewhat advantageous in that pre-cooling increases drying efficiency in the salt bed dryer 20.

As shown in the Figure the dried and cooled myrcene starting material may be passed into a hydrohalogenation apparatus which comprises in the preferred embodiment a stirred tank reactor 40. In reactor 40, hydrohalogenation of the introduced myrcene is carried out in the presence of a catalytic proportion of a hydrohalogenation catalyst, at a temperature within the range of from about −30° C. to about 25° C.; preferably at a temperature within the range of from −10° C. to 25° C., most preferably about 10° C. Hydrohalogenation may be effected, for example, by reaction myrcene with a hydrogen halide like hydrogen chloride or hydrogen bromide, in substantially anhydrous form and under substantially anhydrous conditions, i.e. having less than about 5% water present in the reaction mixture. As shown in the Figure, the preferred hydrohalogenation is with gaseous hydrogen chloride which is introduced as a gas, possibly generated in a vaporizer, and then metered into the reactor 40, via appropriate conduits. Advantageously, the hydrogen chloride is metered into the reactor 40 at a rate of from about 2.0 to about 300 gms/hour/mole of myrcene present in the reactor 40. Preferably, the rate is from about 4.0 to 8.0 gms/hour/mole of myrcene.

The organic amine is introduced into the reactor 40 from storage vessel 50. Myrcene, amine, hydrogen chloride and copper catalyst are introduced into the reactor 40 sequentially. Preferably, the reactor 40 after purging with an inert gas such as nitrogen is first charged with the cool myrcene, the copper catalyst, and the organic amine. While cooling and stirring, the hydrogen chloride is added incrementally to the charge.

A wide variety of catalysts for hydrohalogenation of myrcene are well known and include, for example, any copper-containing compound having a valency of 2 or less, including metallic copper. Any copper compound convertible to the halide such as the bromide, iodide or chloride under conditions of the reaction may also be used. Representative of copper catalysts advantageously employed are the chloride, bromide, carbonate, oxide, acetate, formate, sulfate, and like derivative cupric and cuprous compounds. Preferred as the hydrochlorination catalyst in the improved process of the invention is cuprous chloride. Catalytic proportions of the anhydrous hydrohalogenation catalyst are generally within the weight range of from about 0.01 to 10 percent of the dry myrcene, preferably about 0.5 percent.

Organic amines are generally well-known in the art as is their preparation and include primary, secondary and tertiary amines. Representative of organic amines which may be used in the process of the invnntion are those of the formula:

(VII)

wherein $R_1$, $R_2$ and $R_3$ are each independently selected from the group consisting of hydrogen and hydrocarbyl, at least two of $R_1$, $R_2$ and $R_3$ being hydrocarbyl and containing at least 6 carbon atoms.

The term "hydrocarbyl" as used herein means the monovalent moiety obtained upon removal of a hydrogen atom from a parent hydrocarbon. Representative of hydrocarbyl are alkyl of 1 to 25 carbon atoms, inclusive, such as methyl, ethyl, propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomeric forms thereof; aralkyl of 7 to 25 carbon atoms, inclusive, such as benzyl, phenethyl, phenpropyl, phenbutyl, phenhexyl, napthoctyl and the like; cycloalkyl of 3 to 8 carbon atoms, inclusive, such as cyclopropyl, cyclobutyl, cyclopentyl, cyclohexyl, cycloheptyl, cyclooctyl and the like; alkenyl of 2 to 25 carbon atoms, inclusive, such as vinyl, allyl, butenyl, pentenyl, hexenyl, octenyl, nonenyl, decenyl, undececyl, dodecenyl, tridecenyl, pentadecenyl, octadecenyl, pentacosynyl and isomeric forms thereof.

Organic amine compounds of the formula (VII) given above are generally well-known as are methods of their preparation. Representative of such organic amine compounds are:
Di-n-hexylamine
Dicyclohexylamine
Trihexylamine
Distearylmethylamine
Tri-n-octylamine
Dibenzylamine
and the like.

Preferred compounds of the formula (VII) are those wherein $R_1$, $R_2$ and $R_3$ are alkyl groups and at least two contain from 8 to 22 carbon atoms each.

It will be appreciated that under specific conditoons of operating the process of the invention, certain of the above described compounds of the formula (VII) given above have advantages over other compounds of the same general formula. Selection of a particular compound (VII) for use under specific process cnnditions, for optimum yields may be made by trial and error technique.

The organic amine is used in a proportion to isomerize, during the hydrohalogenation reaction, at least some of the linalyl chloride produced in the method of the invention. Such a proportion is generally within the range of from about 0.01 to 10 percent by weight of the myrcene charge preferably 0.2 to 2.5 percent. Optimum proportions will depend to some extent upon the amine selected and may be determined by trial and error technique.

The controlling reaction rate in the hydrohalogenation process of the invention is the isomerization of the more-substituted halide to the desired less-substituted halide. This is controlled by residence time in the hydrohalogenation reaction zone. We have found that the in hydrochlorination of myrcene, the preferred minimum total residence time is within the range of from 3 to 15 hours, and most preferably 5 to 8 hours under the above described operating temperatures. The presence of linalyl chloride in the reaction mixture may be monitored by conventional analytical techniques. Longer residence times in the hydrochlorination reactor may cause a yield loss due to conversion of the monochlorides to alpha-terpinyl chloride. Shorter residence times may not be sufficient to isomerize the linalyl chloride to the desired geranyl/neryl chlorides.

When it has been determined that hydrohalogenation has occurred to a maximum desired point, the hydrohalogenation product mixture is passed from the hydrohalogenation apparatus.

The following examples describe the manner and process of making and using the invention and set forth the best mode contemplated by the inventors of carrying out the invention but are not to be construed as limiting. All parts given are by weight unless otherwise indicated.

EXAMPLES 1-7

To a 1 liter reaction vessel was charged 300.0 g myrcene (72 wt %), 1.0 g cuprous chloride and an amine as described in Table 1. The mixture was purged with nitrogen and cooled to 0° C. Hydrogen chloride gas was added at a rate of 7-8 g/hour while maintaining the temperature at 10° C. At the end of the reaction (7 hours), monitored by infrared spectroscopy to a 1% myrcene level, the reaction product was neutralized with sodium carbonate and aqueous sodium hydroxide. The product was analyzed by gas chromatography. The results are shown in Table 1. Linalyl, neryl and geranyl chlorides are abbreviated LC1, NC1, and GC1 respectively.

TABLE 1

| Example No. | Amine Used | Molar Yield of Products (%) | | GCl:NCl Ratio |
|---|---|---|---|---|
| | | LCl | NCl + GCl | |
| 1 | None | 18 | 69 | 1.26 |
| 2 | Trihexylamine, 2.7 g | 13 | 78 | 1.59 |
| 3 | Trioctylamine, 3.5 g | 12 | 77 | 1.60 |
| 4 | Adogen 364*, 3.9 g | 10 | 81 | 1.54 |
| 5 | Tri(tridecyl)-amine, 5.7 g | 14 | 78 | 1.82 |
| 6 | Dihydrogenated tallow methyl-amine, 5.1 g | 9 | 81 | 1.76 |
| 7 | Distearyl methyl-amine, 5.5 g | 15 | 71 | 1.41 |

*A mixture of trialkylamines where the alkyl chains comprise 59% $C_8$; 39% $C_{10}$; 1% $C_{12}$ and 1% $C_6$; Sherex Chemical Company.

What is claimed:

1. A novel method for the hydrohalogenation of a myrcene comprising hydrohalogenating myrcene under anhydrous, liquid phase conditions in the presence of a copper-containing hydrohalogenation catalyst, and further comprising carrying out the hydrohalogenation at a temperature of from −10° C. to 25° C. in the presence of an organic amine wherein the amine is selected from the group consisting of aliphatic secondary and tertiary amines containing at least 2 hydrocarbyl groups of six or more carbon atoms each.

2. The method of claim 1 wherein the organic amine contains at least 2 alkyl chains of from 8 to 22 carbon atoms each.

3. The improved method of claim 1 wherein the organic amine is distearylmethylamine.

4. The improved method of claim 1 wherein the organic amine is di(hydrogenated-tallow)methylamine.

5. The improved method of claim 1 wherein the organic amine is a tertiary amine selected from the group consisting of trihexylamine, trioctylamine, tridecylamine tri(dodecyl)amine, tri(tridecyl)amine and a mixture of tri(alkyl)amines wherein the alkyl chains each consist of 8–10 carbon atoms.

6. The improved process of claim 1 wherein the temperature of reaction is preferably from about −10° C. to about 20° C.

7. The process of claim 1 wherein the hydrohalogenation catalyst is cuprous chloride.

8. The process of claim 7 wherein the catalytic proportion of copper-containing catalyst is preferably within the weight range of about 0.01 to about 10.0 percent of the dry myrcene.

9. The process of claim 1 wherein the hydrohalogenation is preferably carried out for a period of from about 3 to about 15 hours.

10. The process of claim 1 wherein the molar ratio of amine to copper catalyst is preferably within the range of from about 0.1 to about 5.0.

* * * * *